(12) United States Patent
Suzuki

(10) Patent No.: US 10,233,560 B2
(45) Date of Patent: *Mar. 19, 2019

(54) METHOD FOR THE PRODUCTION OF SINGLE CRYSTALLINE TIO₂ FLAKES

(71) Applicant: MERCK PATENT GMBH, Darmstadt (DE)

(72) Inventor: Ryuta Suzuki, Fukushima-ken (JP)

(73) Assignee: MERCK PATENT GmbH, Darmstadt (DE)

( * ) Notice: Subject to any disclaimer, the term of this patent is extended or adjusted under 35 U.S.C. 154(b) by 186 days.

This patent is subject to a terminal disclaimer.

(21) Appl. No.: 15/038,313

(22) PCT Filed: Nov. 20, 2014

(86) PCT No.: PCT/EP2014/003098
§ 371 (c)(1),
(2) Date: May 20, 2016

(87) PCT Pub. No.: WO2015/090499
PCT Pub. Date: Jun. 25, 2015

(65) Prior Publication Data
US 2016/0289859 A1    Oct. 6, 2016

(30) Foreign Application Priority Data

Dec. 20, 2013   (EP) .................................. 13005966

(51) Int. Cl.
| | | |
|---|---|---|
| *C30B 1/00* | (2006.01) | |
| *C30B 1/10* | (2006.01) | |
| *A61K 8/29* | (2006.01) | |
| *A61Q 1/02* | (2006.01) | |
| *A61Q 17/04* | (2006.01) | |
| *A61K 8/02* | (2006.01) | |
| *C30B 7/04* | (2006.01) | |
| *C30B 9/12* | (2006.01) | |
| *C30B 29/16* | (2006.01) | |
| *C30B 29/64* | (2006.01) | |
| *B01J 21/06* | (2006.01) | |
| *B01J 35/00* | (2006.01) | |
| *C09D 1/00* | (2006.01) | |
| *C09D 11/00* | (2014.01) | |

(52) U.S. Cl.
CPC .............. *C30B 1/10* (2013.01); *A61K 8/0254* (2013.01); *A61K 8/29* (2013.01); *A61Q 1/02* (2013.01); *A61Q 17/04* (2013.01); *B01J 21/063* (2013.01); *B01J 35/004* (2013.01); *C09D 1/00* (2013.01); *C09D 11/00* (2013.01); *C30B 7/04* (2013.01); *C30B 9/12* (2013.01); *C30B 29/16* (2013.01); *C30B 29/64* (2013.01); *A61K 2800/412* (2013.01)

(58) Field of Classification Search
CPC .................................................. C01G 23/047
See application file for complete search history.

(56) References Cited

U.S. PATENT DOCUMENTS

| | | | |
|---|---|---|---|
| 2,044,941 A | * | 6/1936 | Hanahan |
| 3,579,310 A | * | 5/1971 | Lewis |
| 3,650,693 A | * | 3/1972 | Borchardt |
| 6,627,336 B1 | | 9/2003 | Ohmori et al. |
| 6,908,881 B1 | | 6/2005 | Sugihara |
| 7,084,179 B2 | | 8/2006 | Ohmori et al. |
| 2005/0079367 A1 | | 4/2005 | Ohmori et al. |
| 2007/0292339 A1 | | 12/2007 | Kenji et al. |
| 2009/0117383 A1 | | 5/2009 | Isobe |

FOREIGN PATENT DOCUMENTS

| | | |
|---|---|---|
| EP | 0779243 A1 | 6/1997 |
| EP | 0779243 B1 | 6/2000 |
| EP | 1083152 A1 | 3/2001 |
| EP | 1125636 A1 | 8/2001 |
| FR | 2936513 A1 | 4/2010 |
| GB | 529596 * | 11/1940 |
| JP | S56155098 A | 12/1981 |
| JP | S58-088121 A | 5/1983 |
| JP | S5888121 A | 5/1983 |
| JP | H04-144918 A | 5/1992 |
| JP | H04144918 A | 5/1992 |
| JP | H07002598 A | 1/1995 |
| JP | H07-157312 A | 6/1995 |
| JP | H07157312 A | 6/1995 |
| JP | H09-278442 A | 10/1997 |
| JP | 2004210941 A | 7/2004 |
| JP | 2009-029645 A | 2/2009 |
| WO | 2007102490 A1 | 9/2007 |

OTHER PUBLICATIONS

International Search Report for PCT/EP2014/003098 dated Jan. 23, 2015.
Tobin, L. L. et al, "Characterising dye-sensitized solar cells," Optik, 2011, vol. 122, pp. 1225-1230.
Ciesla, U. et al., "Highly Ordered Porous Zirconias from Surfactant-Controlled Syntheses: Zirconium Oxide-Sulfate and Zirconium Oxo Phosphate," Chem. Mater., 1999, vol. 11, pp. 224-234.
English Abstract for JPH07157312, Publication Date: Jun. 20, 1995.
English Abstract for JPH04144918, Publication Date: May 19, 1992.
English Abstract of JPS5888121, Publication Date: May 26, 1983.
English Abstract of JP2004210941, Publication Date: Jul. 29, 2004.
English Abstract of FR2936513, Publication Date: Apr. 2, 2010.
Office Action in corresponding JP 2016-541094 dated Jun. 19, 2018 (pp. 1-2).

* cited by examiner

*Primary Examiner* — Steven J Bos
(74) *Attorney, Agent, or Firm* — Millen White Zelano & Branigan

(57) ABSTRACT

The present invention is related to a method for the production of single crystalline TiO₂ flakes in the rutile crystal structure, to single crystalline TiO₂ flakes obtained by this method as well as to the use thereof, especially as pigments in several application media.

12 Claims, 3 Drawing Sheets

＃ METHOD FOR THE PRODUCTION OF SINGLE CRYSTALLINE $TiO_2$ FLAKES

BACKGROUND OF THE INVENTION

1. Field of the Invention

The present invention relates to a method for the production of single crystalline $TiO_2$ flakes, to single crystalline $TiO_2$ flakes produced by this method as well as to the use thereof, in particular as pigments.

2. Description of the Related Art

Titanium dioxide ($TiO_2$) is widely used in various fields such as pigments, photo catalysts, solar cells, UV absorbents and water repellants, and various methods have been developed in order to find appropriate methods for producing $TiO_2$, especially in its rutile crystal form.

For example, Japanese Unexamined Patent Application Publication No. 58-88121 (Patent Document 1) discloses a method to obtain titanium dioxide particles of the rutile type which are grown in a specific crystal axis direction, wherein potassium titanate ($K_2O.nTiO_2$) fibers obtained by a flux method are treated with an acid resulting in needle-shaped water containing $TiO_2$-particles which are, in the following, heat treated in order to give rutile $TiO_2$-needles of a very small particle size.

Japanese Unexamined Patent Application Publication No. 04-144918 (Patent Document 2) discloses a method to obtain flaky titanium dioxide particles by dissolving titanium alkoxide and an organic alkaline substance in an organic solvent and forming a film on a belt by coating this solution on a smooth surface, followed by hydrolysis, drying, peeling, and calcination steps.

Japanese Unexamined Patent Application Publication No. 07-157312 (Patent Document 3) discloses a method for obtaining flaky titanium dioxide by acid treatment of potassium di-titanate fibers obtained by a melting method in the presence of a fluxing agent, whereby by means of the acid treatment all of the K+ ions within the crystals are eluted, followed by heat treating the resulting particles to obtain a flake type powder.

However, in the techniques described in these Patent Documents, the obtained particle shape of the titanium dioxide particles may partly not be suitable as pigment, in particular if larger flaky shaped crystals are needed, or the production method should be further improved, especially with respect to energy efficiency, production time and cost.

For example, the titanium dioxide particles obtained by the method described in the Patent Document 1 exhibit a whisker type shape having an extremely fine size (particle diameter of at most 6 μm). Therefore, the use of these particles as pigments is limited, especially with regard to their potential use as highly reflective interference pigments.

Further, although the titanium dioxide particles obtained by the method described in the Patent Document 2 have a flake type shape, they exhibit a polycrystalline structure and the production method is based on organic compounds and solvents which cause high cost and technological efforts and, thus, more complications.

Further, the titanium dioxide particles obtained by the method described in Patent Document 3 exhibit a flake type shape of an appropriate size, but the requirement of two calcination steps takes time and causes high cost and energetic waste in the production procedure.

Thus, the aim of the present invention is to reduce energy cost of the production step and to offer a method to effectively produce single crystalline $TiO_2$ flakes, preferably from inorganic compounds, which are suitable for use as pigments having luster, high refractive index as well as large particle size. A further aim of the present invention is to provide single crystalline $TiO_2$ flakes produced according to said process, as well as to suggest the use thereof.

SUMMARY OF THE INVENTION

The inventors have found that the problems described above can be solved and that single crystalline $TiO_2$ flakes suitable for use as pigments can be effectively produced by mixing a phosphorus compound with a titanium compound in order to form a titanium dioxide precursor, and then by calcinating the obtained precursor, and completed the present invention.

The present invention is following.

(1) A method for the production of single crystalline $TiO_2$ flakes by the following steps:
 1. mixing at least a titanium compound and a phosphorous compound whereby a titanium dioxide precursor is formed; and
 2. calcining the titanium dioxide precursor at a temperature in the range of from 800° C. to 1400° C. as a single calcination step.

(2) The method according to (1), wherein the mixing is executed in an aqueous medium.

(3) The method according to any one of (1) to (2), wherein a fluxing agent is present in the mixing step.

(4) The method according to (3), wherein the fluxing agent is a compound selected from one or more of $Na_2SO_4$, $K_2SO_4$, NaCl and KCl.

(5) The method according to any one of (2) to (4), wherein the method comprises drying of the titanium dioxide precursor prior to the calcination step.

(6) The method according to any one of (1) to (5), wherein the calcining is executed in an oxygen containing atmosphere.

(7) The method according to any one of (3) to (6), wherein a product obtained in the calcination step according to (3) is treated with hot water.

(8) The method according to any one of (1) to (7), wherein the titanium containing compound is a compound selected from one or more of titanium tetrachloride, titanyl sulfate, titanium sulfate and titanium trichloride.

(9) The method according to any one of (1) to (8), wherein the phosphorous compound is a compound selected from one or more of trisodium phosphate, phosphorous pentoxide, phosphoric acid, phosphorous acid and tripotassium phosphate.

(10) Single crystalline $TiO_2$ flakes obtained by the method according to any one of (1) to (9).

(11) Single crystalline $TiO_2$ flakes according to (10), having a rutile crystal structure.

(12) Single crystalline $TiO_2$ flakes according to (10) or (11), having a particle diameter in the range of 10 to 200 μm, according to an equivalent of the corresponding circle diameter.

(13) Single crystalline $TiO_2$ flakes according to any one of (10) to (12), having the shape of a letter "V" when viewed at the largest surface of the flakes.

(14) Use of single crystalline $TiO_2$ flakes according to any one of (10) to (13) in a paint, ink, coating composition, plastic or cosmetic.

(15) Use according to (14) as white pigment, photo catalyst, host material for dye sensitized solar cells, UV absorbent or water repellent.

According to the present invention, a method to effectively produce single crystalline TiO$_2$ flakes which are suitable for use as pigments can be offered.

BEST MODE FOR CARRYING OUT THE INVENTION

Hereinafter, the method for the production of single crystalline TiO$_2$ flakes according to the present invention and the single crystalline TiO$_2$ flakes obtained by this method will be described in detail. However, the present invention is not limited to these particular embodiments as long as the intention of the present invention is followed.

The method for the production of single crystalline TiO$_2$ flakes according to a first embodiment of the present invention (hereinafter, abbreviated to "the production method of the present invention") contains: "a step of mixing at least a titanium compound and a phosphorous compound whereby a titanium dioxide precursor is formed"; and "a step of calcining the titanium dioxide precursor at a temperature in the range from 800° C. to 1400° C. as a single calcination step".

The inventors have found that single crystalline TiO$_2$ flakes suitable for use as pigments can be effectively produced by mixing a phosphorus compound with a titanium compound in order to form a titanium dioxide precursor and then by calcination of the obtained precursor in a single calcination step. The single crystalline TiO$_2$ flakes have a high refractive index and high luster, therefore, they are particularly suitable as highly reflective pigments, especially interference pigments. The production method of the present invention enables an effective production of good quality single crystalline TiO$_2$ flakes with the need for only a single calcination step. Therefore, this method is highly suitable for the suppression of production cost and efforts. Furthermore, it can produce single crystalline TiO$_2$ flakes, in which twin crystals and coagulations hardly occur and in which crystallinity is high and diameter control is possible.

Therefore, single crystalline TiO$_2$ flakes in the rutile form having an extremely high refractive index can be produced.

Although the detailed mechanisms for the formation of single crystalline TiO$_2$ flakes according to the present invention have not been sufficiently clarified, the inventors have confirmed that TiO$_2$ flakes have been formed with a titanium compound under the co-existence of phosphorus ions. Hereinafter, the production method of the present invention will be described in detail.

The production method of the present invention contains as the first step a step of mixing at least a titanium compound and a phosphorous compound whereby a titanium dioxide precursor is formed (hereinafter, abbreviated to the "mixing step").

In the first and most simple embodiment of the present invention, the concrete types for the titanium compound and for the phosphorus compound as well as a concrete method for mixing are not limited to any specifics as long as a titanium dioxide precursor can be formed. Since the formation of a titanium dioxide precursor will occur even if pure titanium is used, the titanium dioxide precursor is formed independently of the kind of starting materials for the titanium compound and the phosphorous compound, respectively. Here, the "titanium dioxide precursor" is considered to contain titanium oxide hydrate as the mayor component.

As a second step, the production method according to the present invention contains a step of calcining the titanium dioxide precursor at a temperature in the range of from 800° C. to 1400° C. as a single calcination step (hereinafter, abbreviated to the "calcination step").

Anatase type TiO$_2$ is transformed into the rutile type by calcination of a titanium oxide precursor at a temperature of at least 800° C. Since rutile TiO$_2$ flakes are preferred according to the present invention, the minimum calcination temperature in the present calcination step is 800° C. Calcination of a titanium dioxide precursor at a temperature of more than 1400° C. would result in a bar type single crystal TiO$_2$, rather than in the flake type. Therefore, the calcination temperature in the present production method is usually at least 800° C., and more preferably at least 900° C. Also it is usually at most 1400° C. and more preferably at most 1250° C., leading to a preferred temperature range of from 900° C. to 1250° C.

The calcination time should be appropriately selected according to the desired shape of the single crystalline TiO$_2$ flakes (particle diameter, thickness, and aspect ratio). It is usually at least 5 minutes, preferably at least 10 minutes, and more preferably at least 2 hours. Further, this value is usually at most 12 hours, preferably at most 10 hours, and more preferably at most 5 hours.

The calcination atmosphere is not limited to any specifics as long as TiO$_2$ can be formed. However, in order to reliably produce the oxide, the calcination step is preferably carried out under oxygen containing atmosphere.

The concrete method for mixing of the titanium compound and phosphorus compound at the mixing step is not limited to any specifics, however, they are preferably mixed in an aqueous medium because working in aqueous solution is comfortable and easy to handle. If the mixing step according to the present invention is executed in an aqueous medium, this variation of the present process represents the second embodiment of the present invention.

The addition of the phosphorus compound to the aqueous medium may be carried out prior to the addition of the titanium compound, at the same time as the addition of the titanium compound, or after the addition of the titanium compound. However, when the phosphorus compound is added to the aqueous medium prior to the addition of the titanium compound, the yield of the TiO$_2$ flakes may be increased. Therefore, the latter sequence is preferred.

When the mixing is carried out within an aqueous medium, it is preferred to hold the aqueous solution at a pH value in the region of from pH 6 to 8 in order to avoid damage to the crucible by gas generated during calcining. For example, when an acidic titanium compound such as titanium tetrachloride is added to the aqueous solution containing a basic phosphorus compound such as trisodium phosphate, this solution is neutralized fully or at least to a certain degree.

Further, the pH value may be adjusted to pH 6 to 8 by separately adding an acidic solution such as hydrochloric acid or sulfuric acid or a basic solution such as sodium hydroxide aqueous solution or sodium carbonate. Furthermore, it is desirable for the addition of the titanium compound to be carried out gradually over a longer time period in order to suppress a rapid pH variation.

According to the present invention, the "aqueous medium" indicates a medium mainly comprising tap water or purified water and it may also be an aqueous solution comprising another component in addition or alternatively to the pure water such as deionized water.

According to a third embodiment of the present invention, it is preferred that a fluxing agent is added to the above mentioned starting materials prior to the calcination step. Here, the "fluxing agent" indicates a type of compound, in particular a metal salt, that functions as a dissolution means in a so called "fluxing growth process", which leads to the formation of $TiO_2$ from the titanium dioxide precursor at the calcination step.

For being useful as a fluxing agent in the production process according to the present invention, the corresponding metal salts should exhibit a melting temperature which is not less than 800° C. but does not achieve or exceed the melting temperature of the resulting $TiO_2$. In addition, they have to be water soluble. Examples are metal salts such as $Na_2SO_4$, $K_2SO_4$, NaCl and KCl, either alone or in combination of two or more thereof, whereby KCl may only be used in combination with at least one of the other salts mentioned. From the view point of cost and ready availability, $Na_2SO_4$ and $K_2SO_4$ are preferred, and $Na_2SO_4$ is particularly preferred.

Since the addition of a fluxing agent influences the crystal growth process of the resulting pigments, the usage amount of the fluxing agent should be appropriately selected according to the desired shape of the single crystal $TiO_2$ flakes (particle diameter, thickness, and aspect ratio). The ratio of the fluxing agent mol number against the Ti atom mol number in the used titanium compound (fluxing agent mol number/Ti atom mol number in the titanium compound), it is usually at least 1.0, and more preferably at least 3.0. Further, this value is usually at most 30, and more preferably at most 10. In case of a ratio of less than 1.0, the fluxing salt treatment effect would be insufficient. On the other hand, if the ratio would exceed the value of 30, no further improvement in the flake formation would occur and a larger scale washing step to eliminate them later would be necessary.

The addition of the fluxing agent into the mixture of the starting materials may be executed prior to the addition of the titanium compound, at the same time as the addition of the titanium compound, or after the addition of the titanium compound. However, when the fluxing agent is added after the addition of the titanium compound, the yield of the $TiO_2$ flakes may be increased. Therefore, the latter adding sequence is particularly preferred.

The production method according to the present invention may preferably also contain other steps, in addition to the mixing step and calcination step. This belongs to the following steps:

drying step of the titanium dioxide precursor, in order to obtain a powder of the molten salt mixture prior to the calcination step (hereinafter, abbreviated to "drying step 1"); The temperature in drying step 1 is preferably in the range of from 70° C. to 180° C., although the method is not limited to this.

in order to remove impurities such as chloride, sulfate, etc. from the product obtained in the calcination step, a step to treat the product obtained at the calcination step with warm water (hereinafter, abbreviated to "washing step"); Warm water used at the washing step is not limited to any specifics, however, purified water and deionized water are preferred. Here, the temperature of the warm water is preferably in the range of from 40° C. to 100° C. In case that a fluxing agent is used for the present production method, such a washing step is indispensable.

in order to separate the $TiO_2$ flakes from the solution containing dissolved impurities after the washing step, a step to filter and separate the undissolved solids (the $TiO_2$ flakes) after the washing step (hereinafter, abbreviated to "filtration step"); and in order to dry the $TiO_2$ flakes, a step to dry the $TiO_2$ flakes (hereinafter, abbreviated to "drying step 2"). This drying step is executed preferably in a temperature range of from 20° C. to 180° C., although the present process is not limited thereto.

Regarding the titanium compound which may be used as a starting material for the present production method, water soluble titanium compounds are preferred, in particular in case the process is executed in an aqueous medium. Organic titanium compounds as well as inorganic titanium compounds may be used, but inorganic titanium compounds are clearly preferred. Using water soluble inorganic titanium compounds makes the production process simple and easy to handle, in combination with no need for expensive apparatuses and explosion protection.

Inorganic titanium compounds are preferably inorganic titanium salts. Examples of titanium salts are: titanium tetrachloride, titanium oxy sulfate, titanium sulfate and titanium tri-chloride. However, from the view point of the cost and ready availability, titanium tetra-chloride and titanium sulfate are preferred. Here, the type of the used titanium compound is not limited to one type and at least two types may be used together.

The usage amount of the titanium compound should be appropriately selected according to the desired amount of the single crystalline $TiO_2$ flakes to be produced. As the ratio of Ti atom mol number in the single crystalline $TiO_2$ flakes against the mol number in the used titanium compound (Ti atom mol number in the single crystalline $TiO_2$ flakes/Ti atom mol number in the titanium compound), it is usually at least 0.3, preferably at least 0.4 and more preferably at least 0.5. Further, this value is usually at most 0.9, preferably at most 0.95 and more preferably at most 1.0.

As the phosphorus compound, phosphate compounds such as phosphoric acid, phosphates, condensed phosphoric acid, and condensed phosphate may be listed, and any one can be used as long as it is water soluble. Among them, from the view point of cost and ready availability, trisodium phosphate, phosphorus pentoxide, phosphoric acid, phosphorous acid, and tri-potassium phosphate are preferred. Trisodium phosphate is particularly preferred. Here, the types of the used phosphorus compound is not limited to one type and at least two types may be used together.

The usage amount of the phosphorus compound should be appropriately selected according to the desired shape of the single crystal $TiO_2$ flakes (particle diameter, thickness, and aspect ratio). As the ratio of phosphorus compound mol number against the Ti atom mol number in the used titanium compound (phosphorus compound mol number/Ti atom mol number in the titanium compound), it is usually at least 0.01, preferably at least 0.1, and more preferably at least 1.0. Further, this value is usually at most 10, preferably at most 7.0, and more preferably at most 5.0.

According to the present production process, single crystalline $TiO_2$ flakes of high quality may be effectively produced. Thus, a further object of the present invention is single crystalline $TiO_2$ flakes produced by the process mentioned above.

The single crystalline $TiO_2$ flakes according to the present invention usually exhibit the shapes and sizes as described below, although they are not limited thereto.

The average particle diameter of the $TiO_2$ flakes is usually at least 10 µm, preferably at least 15 µm. And this value is usually at most 200 µm, preferably at most 150 µm.

As soon as the average particle diameter of the $TiO_2$ flakes is within the region mentioned above, it is possible to obtain a pigment having high luster. Here, the "average particle diameter" expresses a diameter of a circle corresponding to the largest length or width of the flake, and indicates the average value obtained from the particle size distribution based on the volume.

The thickness of the flakes is usually at least 0.1 μm, preferably at least 0.2 μm. And this value is usually at most 2.0 μm, preferably at most 1.0 μm. As long as the thickness is within this region, pearl luster of the resulting $TiO_2$ flakes may occur, optionally in combination with interference colour, depending on the actual thickness of the flakes.

The aspect ratio of the flakes is usually at least 5, preferably at least 7.5. This value is usually at most 150, preferably at most 100. A high aspect ratio leads to good orientation and thus, high luster, of the resulting $TiO_2$ flakes in any coating layer to which they might be added.

The crystal structure of the $TiO_2$ flakes according to the present invention is preferably the rutile type. Rutile $TiO_2$ is known to exhibit a high refractive index and, since the $TiO_2$ particles exhibit a flaky shape, also to exhibit high luster.

By means of the production method according to the present invention, for example, particles as shown in FIGS. 1 (a) and (b) are obtained. The particles are separated by a border line as shown in FIG. 1 (c). After being physically separated from each other, the single crystalline $TiO_2$ flakes have a shape as shown in FIG. 2 (a) "V letter" type or (b) "triangle" type. The single crystalline $TiO_2$ flakes have a "V"-letter like shape and "triangle" like shape when the largest surface of the flake is observed, as shown in FIGS. 3 and 4. Therefore, the single crystalline $TiO_2$ flakes may exhibit a relatively large surface and, thus, a good orientation in the application medium.

The single crystalline $TiO_2$ flakes of the present invention are suitable as pigments, particularly for paints, inks, coating compositions, plastics or cosmetics. Therefore, the use of the present single crystalline $TiO_2$ flakes as pigments in paints, inks, coating compositions, plastics or cosmetics also one object of the present invention. Further, as the single crystalline $TiO_2$ flakes of the present invention have either a higher refractive index and/or better luster than traditional $TiO_2$ particles or flakes, they may also advantageously be used as photo catalysts, host material for dye sensitized solar cells, UV absorbents, water repellents and in all other applications where $TiO_2$ flakes may usually be used.

In this photograph and schematic view, the single crystalline $TiO_2$ flakes of the V letter type (a), the single crystalline $TiO_2$ flakes of the triangle type (b) and a border line between V letter and triangle (c) are shown.

Figure 1:
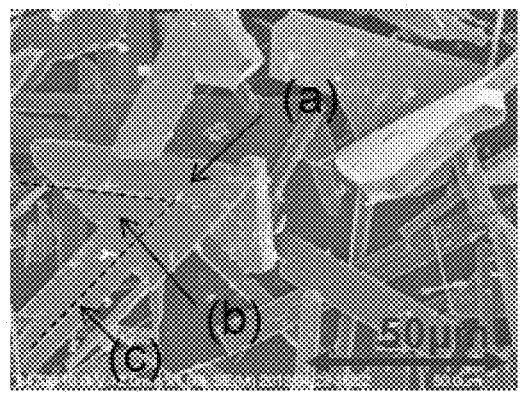
FIG. 1 is a SEM image of the surface of single crystalline $TiO_2$ flakes obtained by the production method in accordance with an embodiment of the present invention.
Figure 2:
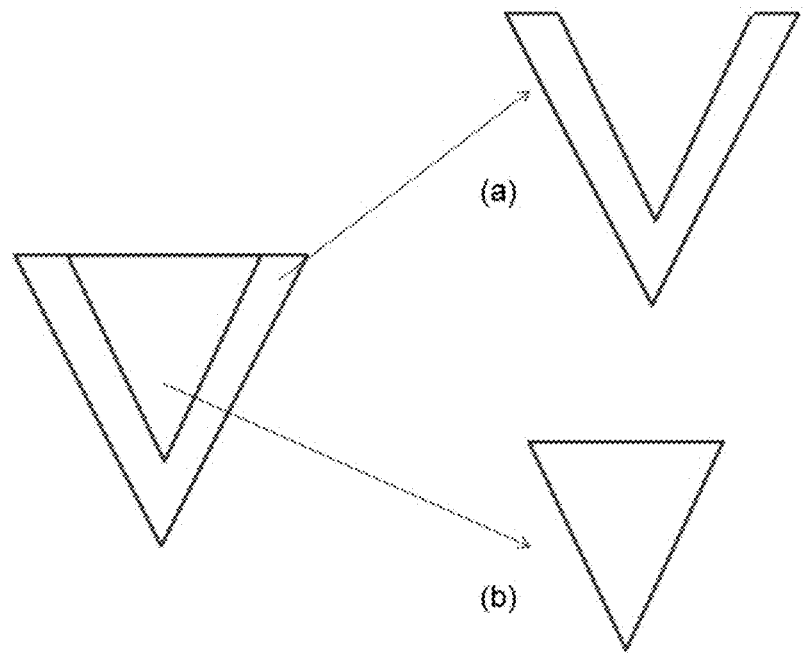
FIG. 2 is a schematic view showing a formation state of the single crystalline $TiO_2$ flakes (V letter type and triangle type) obtained by the production method in accordance with an embodiment of the present invention.
Figure 3:
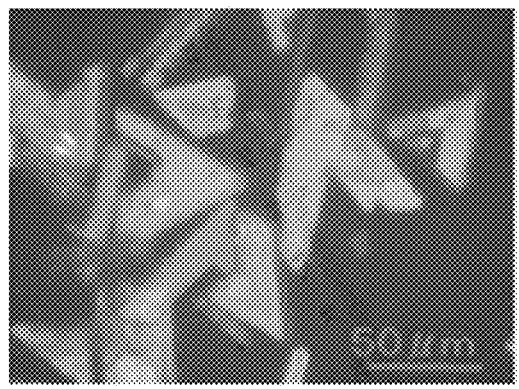

FIG. 3 is a SEM image of the surface of single crystalline $TiO_2$ flakes (V letter type) obtained by the production method in accordance with an embodiment of the present invention.

Figure 4:
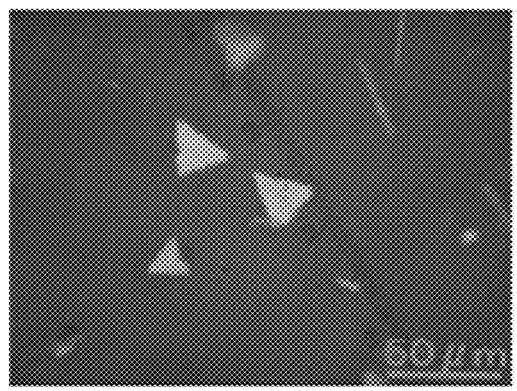

FIG. 4 is a SEM image of the surface of single crystalline $TiO_2$ flakes (triangle type) obtained by the production method in accordance with an embodiment of the present invention.

Figure 5:
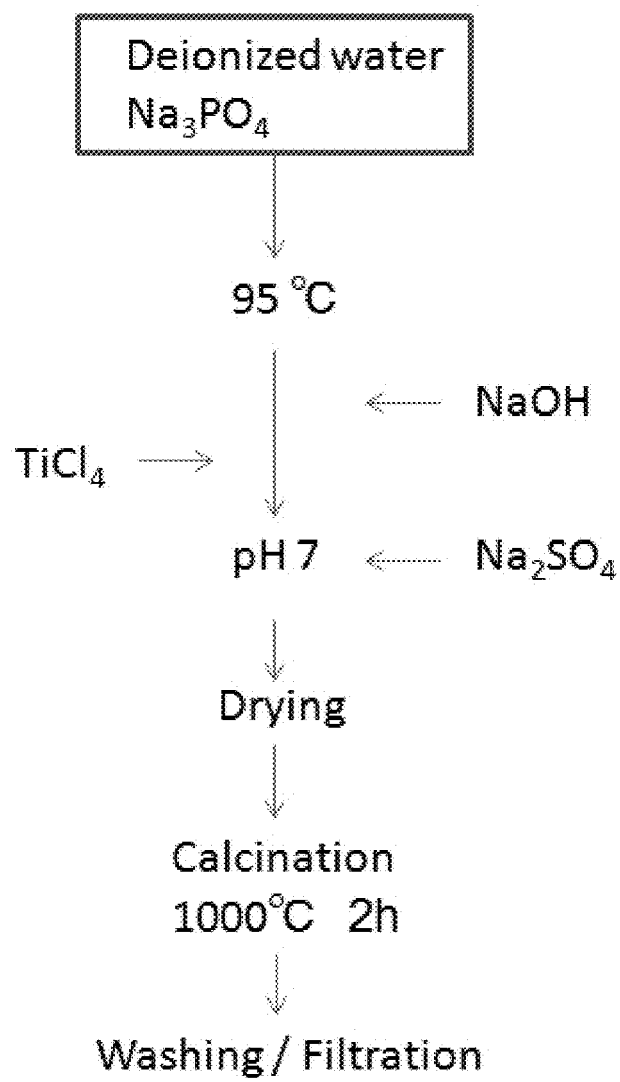

FIG. 5 is a flowchart showing the production method for single crystalline $TiO_2$ flakes in accordance with a preferred embodiment of the present invention.

Hereinafter, the present invention will be described in more detail by referencing examples, however, the present invention is not limited to these examples.

EXAMPLE 1

Into 1600 g of deionized water, 5.6 g of sodium phosphate is added and stirred while heating to 95° C. Into this solution, 200 g of titanium tetrachloride solution (32.0% concentration) is added over the course of two hours while adjusting the pH with sodium hydroxide aqueous solution (32.0% concentration). After adding all of titanium tetra-chloride solution, the pH is raised to 7. Further, 130 g of sodium sulfate is added under stirring. Afterwards, the resulting solution is dried and, then calcined at 1000° C. for two hours. After cooling, the obtained product is washed within warm water under agitation in order to remove chloride and sodium sulfate, and the $TiO_2$ flakes are obtained.

The obtained $TiO_2$ flakes have an average particle diameter of 70 μm and most of them exhibit the V-like shape. From the X-ray diffraction analysis, the main surface of the flake have the (110) orientation and the crystal structure is the rutile type. Further, the analysis with electron microscope confirms that they are single crystals.

The obtained $TiO_2$ flakes are added into a usual nitro-cellulose lacquer in an amount of 5% by weight, in relation to the total weight of the mixture. The resulting coating composition containing the obtained $TiO_2$ flakes is coated onto paper, resulting in a lustrous coating after drying. The $TiO_2$ flakes prepared according to Example 1 present the strongest luster among the examples.

EXAMPLE 2

Into 600 g of deionized water, 5.6 g of sodium phosphate is added and stirred while heating to 95° C. Into this solution, 200 g of titanium sulfate solution (32.0% concentration) is added over the course of two hours while adjusting the pH with sodium hydroxide aqueous solution (32.0% concentration). After adding all of titanium sulfate solution, the pH is raised to 7. Further, 130 g of sodium sulfate is added under agitation and the resulting solution is dried. Then, the obtained powder is calcined at 1000° C. for two hours. After cooling, the obtained product is washed within warm water under agitation in order to remove sulfate and sodium sulfate, and $TiO_2$ flakes having the rutile type crystal structure are obtained. The average particle diameter is 45 μm.

The obtained $TiO_2$ flakes are added into the nitro-cellulose lacquer in an amount of 5% by weight, based on the total weight of the mixture. The obtained coating composition containing the $TiO_2$ flakes are coated on paper and then the luster of the dried coating is observed. The coating shows a sufficient luster in a somewhat smaller degree than the coating according to example 1.

COMPARATIVE EXAMPLE

Deionized water (600 g) is heated to 95° C. Into this, 200 g of titanium tetrachloride solution (32.0% concentration) is added over the course of two hours while adjusting the pH with sodium hydroxide aqueous solution (32.0% concentration). After adding all of titanium tetra-chloride solution, the pH is raised to 7. Further, 130 g of sodium sulfate is added and the resulting solution is stirred and then dried. Then, the resulting powder is calcined at 1000° C. for two hours. After cooling, the obtained product is washed within warm water under agitation in order to remove chloride and sodium sulfate. $TiO_2$ particles having the rutile type crystal structure are obtained. The obtained particles have an average particle diameter of 6 μm and a fiber-like shape with a granular surface.

The obtained $TiO_2$ particles according to the comparative example are added to the nitro-cellulose lacquer in an amount of 5% by weight, based on the total weight of the coating composition. The obtained coating composition containing the $TiO_2$ particles is coated onto paper and observed. There was no specific appearance such as luster.

The single crystal $TiO_2$ flakes obtained by the production method according to the present invention can be utilized as pigments for paints, inks, coating compositions, plastics and cosmetics, and as a photo catalyst, host material for dye sensitized solar cells, UV absorbent or water repellent.

The invention claimed is:

1. Method for the production of single crystalline $TiO_2$ flakes having an average particle diameter in the range of 10 to 200 μm according to the largest length or width of the flake, by the following steps:
   a) mixing at least a water soluble titanium compound and a water soluble phosphorus compound in an aqueous medium at a ratio of the mol number of the phosphorus compound to the Ti atom mol number in the titanium compound in the range of from at least 0.01 to at most 10.0, to form a titanium dioxide precursor, and
   b) calcining the titanium dioxide precursor at a temperature in the range of from 800° C. to 1400° C. as a single calcination step.

2. Method according to claim 1, wherein a fluxing agent is present in the mixing step which is a metal salt that exhibits a melting temperature not less than 800° C. and does not achieve the melting temperature of the resulting $TiO_2$, at a ratio of the fluxing agent mol number to the Ti atom mol number in the titanium compound in the range of from at least 1.0 to at most 30, and wherein a product obtained in the calcination step is washed with water having a temperature in the range of from 40 to 100° C.

3. Method according to claim 2, wherein the fluxing agent is $Na_2SO_4$, $K_2SO_4$, NaCl or KCl.

4. Method according to claim 1, wherein the method comprises drying of the titanium dioxide precursor prior to the calcination step.

5. Method according to claim 1, wherein the calcining takes place in an oxygen containing atmosphere.

6. Method according to claim 1, wherein the titanium compound is titanium tetrachloride, titanyl sulfate, titanium sulfate or titanium trichloride.

7. Method according to claim 1, wherein the phosphorus compound is trisodium phosphate, phosphorus pentoxide, phosphoric acid, phosphorus acid or tripotassium phosphate.

8. A method according to claim 2, wherein the ratio of the fluxing agent mol number to the Ti atom mol number in the titanium compound in the range of from at least 3.0 to at most 10.

9. A method according to claim 1, wherein the ratio of the mol number of the phosphorus compound to the Ti atom mol number in the titanium compound in the range of from at least 1 to at most 7.0.

10. A method according to claim 1, wherein the ratio of the mol number of the phosphorus compound to the Ti atom mol number in the titanium compound in the range of from at least 1 to at most 5.0.

11. A method according to claim 1, wherein the average particle diameter of the $TiO_2$ flakes is usually at least at least 15 μm and at most 150 μm.

12. A method according to claim 1, wherein the thickness of the $TiO_2$ flakes is at least 0.2 μm and at most 2.0 μm and the aspect ratio of the flakes is at least 7.5 and at most 100.

* * * * *